United States Patent [19]

Hawes

[11] 3,972,618

[45] Aug. 3, 1976

[54] INTERFEROMETER FOR TESTING MATERIALS OF DIFFERENT SIZES

[75] Inventor: Roland C. Hawes, Monrovia, Calif.

[73] Assignee: UTI-Spectrotherm Corporation, Santa Clara, Calif.

[22] Filed: Nov. 18, 1974

[21] Appl. No.: 524,649

[52] U.S. Cl. .................. 356/106 R; 356/106 S; 356/244
[51] Int. Cl.² .................. G01B 9/02; G01N 21/16
[58] Field of Search ........... 356/244, 246, 256, 183, 356/51, 207, 208, 96, 106 S; 250/575, 576

[56] References Cited
UNITED STATES PATENTS 3,728,540  4/1973  Todd et al. .................... 356/51
3,753,619  8/1973  Thorpe et al. .................. 356/106 S
3,758,217  9/1973  Stokstad ........................ 356/256

Primary Examiner—John K. Corbin
Assistant Examiner—Conrad Clark
Attorney, Agent, or Firm—Limbach, Limbach & Sutton

[57] ABSTRACT

An interferometer having two spaced apart but parallel composite beams passing through respective fluid containing cells with the radiation output of these cells being imaged onto a detector. The optics at one end of the cells are made movable with respect to the optics at the other end of the cells in order to accommodate various size cells and materials, and to simplify optical alignment of the interferometer without disturbing the focusing properties of the instrument.

6 Claims, 3 Drawing Figures

INTERFEROMETER FOR TESTING MATERIALS OF DIFFERENT SIZES

BACKGROUND OF THE INVENTION

Many varieties of optical instruments exist that provide for passing light or other optically behaved electromagnetic radiation through some material of interest, the material being either in a gaseous, liquid or solid form. An output beam emerging from the material contains information as to its characteristics. Information derived from the output beam is used as part of various analytical procedures. Examples of such instruments include the spectrophotometer, interferometer and spectrometer.

Most of these types of instruments are useful only for a gaseous, liquid or solid material of a single physically contained size. It is a primary object of the present invention to provide an optical instrument of the class described above that is capable of precise analysis of fluids contained within fluid cells of various sizes and shapes, as well as analysis of solids of various shapes.

SUMMARY OF THE INVENTION

This and additional objects are accomplished by the present invention which, briefly, provides for the illuminating optics on one side of the sample material area as a first optical assembly and the detecting optics on the other side of the sample material area as a second optical assembly to be movable back and forth with respect to one another to accommodate various size materials and containing cells without changing the focal characteristics of any of the illuminating or detecting optics. This approach is extremely beneficial in an interferometer that is part of a spectrometer, the example described hereinafter.

In the specific instrument described as a preferred embodiment herein, two spaced apart parallel beams having fixed point foci are generated by an illuminating optical system that is mounted on one base plate. The detector optics and fluid containing cells are mounted on another base plate and provide for imaging two points in space onto a point radiation detector. The two optical mounting base plates are mechanically held in a manner to be accurately slidable with respect to one another over a straight distance that includes not only coincidence of each illuminating beam focus and one of the positions in space imaged by the detector optics but also extends substantially beyond this coincidence position. This system is thus capable of passing the two illuminating beams through a wide range of sizes of fluid containing cells and solid materials placed in the path of the beams by adjusting the relative position of the optics. The optimum adjustment occurs when each illuminating beam point focus is coincident with or imaged onto its associated point in space that is in turn imaged onto the detector. These movable optics also make it easy to make various optical adjustments of the instrument in the absence of any fluid cell or material under test.

Additional objects, advantages and features of the present invention will become apparent from the following description which should be taken in conjunction with the accompanying drawings.

DESCRIPTION OF A PREFERRED EMBODIMENT

Figure 1:
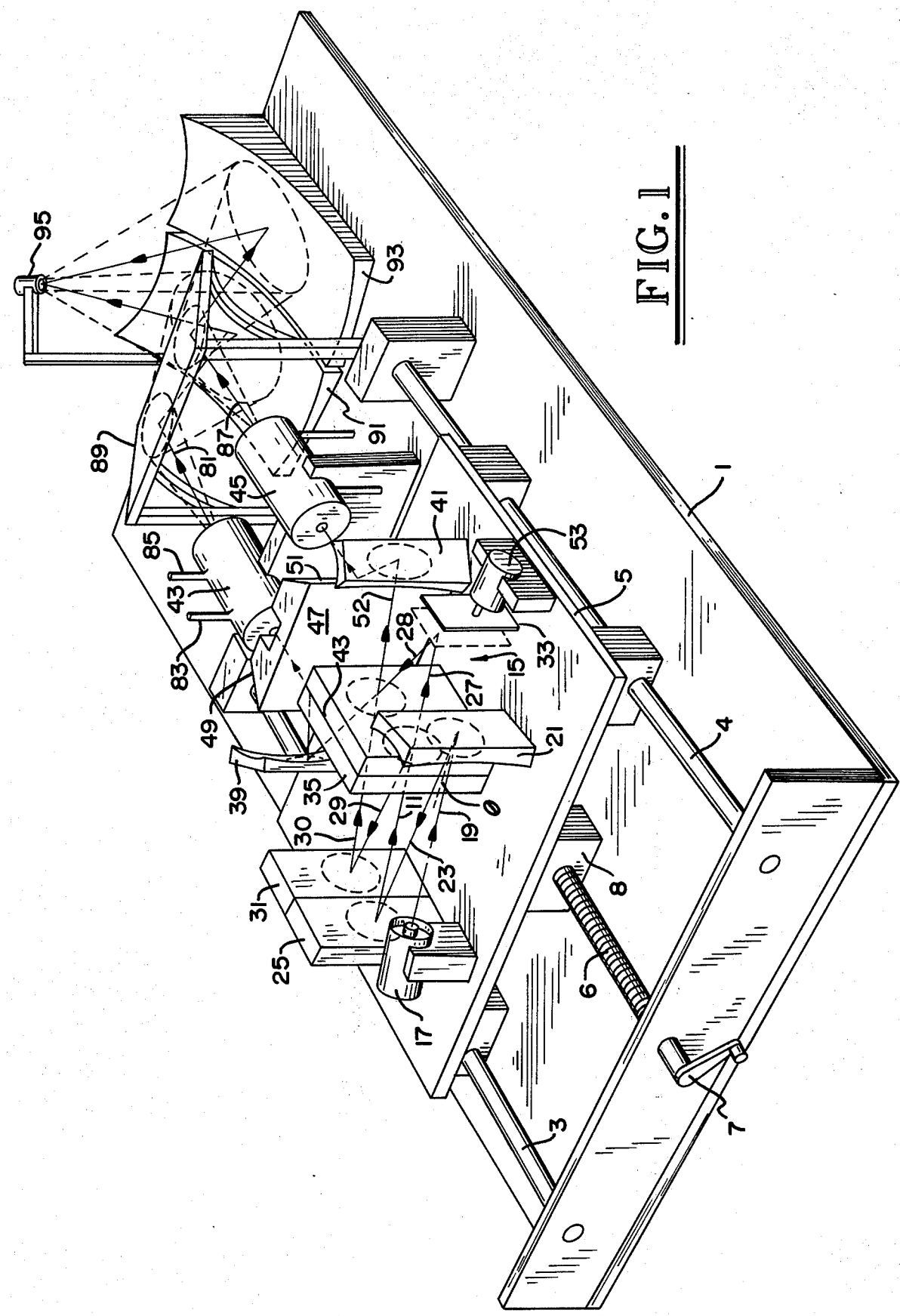
FIG. 1 schematically illustrates a preferred embodiment of the present invention.

Referring initially to FIG. 1, a base plate 1 is provided with an end plate 2. Smooth rods 3 and 4 are held fixed with respect to the base plate 1. A platform 5 is mounted in an appropriate manner on the rods 3 and 4 to be freely slidable back and forth therealong. The rods 3 and 4 are, of course, parallel to one another and held at a uniform distance above the base plate 1 along their lengths. A screw drive member 6 is held by the front plate 2 in a manner to be rotatable with respect thereto but held against axial movement. A crank 7 is fixed to the screw drive 6 for hand rotation of it. A block 8 fixed to the underside of the platform 5 has a threaded aperture that accepts the screw drive 6 so that a turning of the crank 7 causes the platform 5 to move along the support rods 3 and 4.

The movable platform 5 contains, in this example, sample and reference illuminating optics as a first major optical component of an interferometer. The use of the improved adjustable interferometer illustrated in FIG. 1 is principally designed as a component of a spectrometer. The spectrometer is used to determine the spectral characteristics of a material under test as a function of radiation wavelength. The optics of the interferometer that are mounted on the movable platform 5 will now be described in detail.

A collimated electromagnetic energy beam 11 is directed against a planar beam splitting surface 13 with an angle of incidence therebetween indicated by $\theta$. (The angle of incidence is defined as the angle that a beam makes with a line perpendicular to the surface in question). The beam splitting surface 13 is formed by a coating of germanium on joined surfaces of two potassium chloride slabs of equal thicknesses to result in a complete beam splitter 15. This type of structure is commercially available.

The angle $\theta$ is made to be less than about 20°, and in a specific form of this apparatus is 13°. The angle $\theta$ is made as small as possible while still obtaining adequate spatial separation of the split components of the beam 11 so that various optical elements may be positioned in one beam without interferring with an adjacent beam. The small angle has the advantage that both orthogonal states of polarization of the incident radiation beam 11 are similarly reflected and transmitted when passing through the beam splitter 15. Usual interferometers wherein the angle of incidence with a beam splitter is about 45° have the disadvantage that different polarization senses are reflected and transmitted differently when refracted within the beam splitter, resulting in strongly elliptically polarized beams. The result is that the instrument responds to the polarization properties of samples in addition to their absorption properties being investigated. A small angle $\theta$ has the further advantage of contributing to a compact interferometer.

The incident radiation beam 11 is generated by a small area source 17. A diverging radiation beam 19 strikes a mirror element 21 that is shaped to form the radiation into a collimated beam 23. The collimated beam 23 strikes a flat mirror 25 to form the collimated incident radiation beam 11.

In the specific interferometer example being described, the electromagnetic energy source 17 is an infrared source having a useful wavelength range of from about one to 15 microns with a peak energy at about 2.3 microns. Various infrared sources with such a range are available. This range includes wavelengths usually employed in infrared analysis of materials.

The electromagnetic energy beam 11 is incident upon an area of the beam splitting surface 13 that is quite small relative to the entire area of the beam splitting surface. The beam 11 is split into nearly equal intensity beams 27 and 29. The transmitted component 27 of the incident beam 11 strikes a mirror 33 and is thence reflected back to a different area of the beam splitting surface 13 in the form of a beam 28. Similarly, the reflected component 29 of the incident beam 11 is redirected by a mirror 31 positioned in its path to form a reflected beam. The beam 30 is also directed by the mirror 31 to strike the same second area of the beam splitting surface 13 that is illuminated by the beam 28, but on the opposite side of the beam splitting surface 23.

The beams 28 and 30 are thus recombined in well known ways by interaction with the beam splitting surface 13 into two composite beams 35 and 37 having modulated intensities of opposite phase. The composite beams 35 and 37 each contain about one-half of their average intensity from one of the beams 28 and 30 and the other half of their average intensity from the other of the beams 28 and 30. The particular geometric arrangement makes possible the combination of the components of the composite beams 35 and 37 to be coaxially aligned so as to produce desired interference. The composite beam 35 is reflected by a focusing mirror 39 and a composite beam 37 is reflected by a focusing mirror 41.

A mirror structure 47 having reflective surfaces 49 and 51 is also fixed to the platform 5. The result is to direct the composite beams 35 and 37 in parallel paths near to each other. The beam 35 is brought to a focus 73 and the beam 37 to a focus at 74 by their mirrors 39 and 41, respectively. The beams 35 and 37 and their respective foci 73 and 74 then move relative to the base plte 1 as the movable plate 5 is slid along the rods 3 and 4.

The reflective mirror 31 remains fixed with respect to the beam splitter 15 while its counterpart mirror 33 on the opposite side of the beam splitter 15 is given a linear ramp motion in a path away from and toward the beam splitter 15. The mirror 33 is given this oscillation by an appropriate motor source 53. The motor 53 is fixed with respect to the plate 5 but the mirror 33 is not. A total movement of the mirror 33 of a little over one millimeter is utilized in a preferred embodiment. A range of 1-5 millimeters operates quite satisfactorily in the optical system described herein. The motion of the mirror 33 follows the path of a sawtooth waveform; that is, the velocity of the mirror in one direction with respect to the beam splitter 15 is uniform over its path of one millimeter in one direction with a sudden return of the mirror 33 to its beginning position. One full cycle of the mirror 33 takes about 2½ seconds. This repetitive oscillatory mirror motion encodes the radiant energy by intensity modulation at audio frequencies without a need for mechanically chopping a beam as is done in many existing interferometers.

The composite beam 35 is thus composed of approximately one-half of its intensity of light as reflected by the moving mirror 33 and the remaining approximately one-half of the intensity as reflected by the fixed mirror 31. These two components of the beam 35 interfer with each other in a manner determined by their spectral content and a relative path length difference caused by motion of the mirror 33. The composite beam 37 has similar characteristics.

Each of the composite beams 35 and 37 are passed through respective individual fluid containing cells 43 and 45. The cells 43 and 45 are held fixed with respect to the base plate 1. A frequent use of spectrometers involves the analysis of materials in a gaseous state. Such sample materials are generally diluted by some carrier gas which is of no interest. Therefore, the use of two cells 43 and 45 permits one of the cells, for example the fluid cell 43, to act as a "reference" cell and the other cell 45 to be a "sample" cell. The reference cell is made to contain the same materials as the sample cell 45 except for the particular gaseous sample to be analyzed. The result of the interferometer is to form an interferogram of only the sample material without any distortion by carrier gases, etc., that might be mixed with the sample. Furthermore, the use of a reference cell as well as the sample cell permits cancellation of the effect of windows and other light modifying elements of the cells themselves since the reference cell will be approximately the same in these respects as the sample cell.

Figure 2:
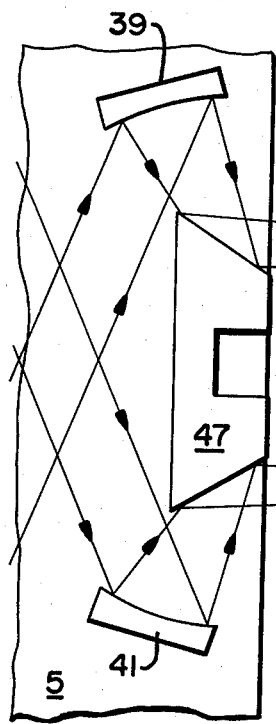
FIG. 2 shows in plan view a portion of the optical system of FIG. 1.
Figure 2:
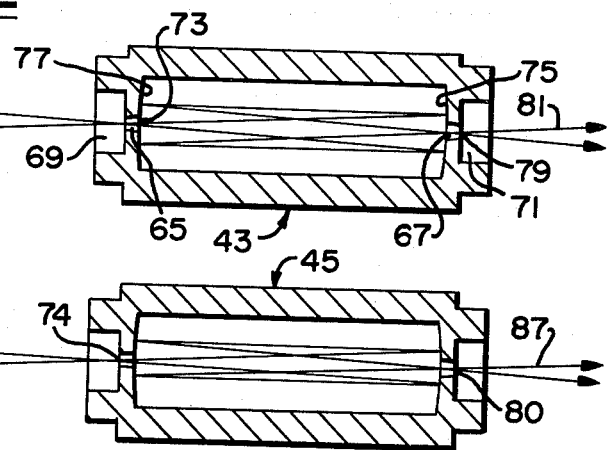

FIG. 2 shows each of the fluid containing cells 43 and 45 in a cross-sectional view. The cell 43 will be described. The cell 45 is of the same construction. A fluid chamber is formed by a casing having a small input aperture 65 and a small output aperture 67 located on opposite side walls of the fluid chamber for permitting light to pass through the material under investigation. These apertures are covered by windows 69 and 71 respectively in order to keep fluid from leaking out of the internal chamber. For infrared radiation, the windows 69 and 71 are preferably potassium chloride. The point focus 73 of the composite radiation beam 35 is positioned at the input of the narrow aperture 65.

Radiation entering through the aperture 65 travels across the fluid chamber as a diverging beam until it strikes a concave reflective surface 75 at the opposite end. The surface 75 is shaped to direct the energy back across the cell to a similar concave reflective surface 77 in a collimated beam. The reflective surface 77 then converges the collimated beam to a point focus 79 at the exit aperture 67 to form an output beam 81. The output beam 81 thus contains the radiation absorption spectrum of the material within the fluid cell 43. The apertures 65 and 67 are made as small as possible to minimize radiation loss from the cell. The mirrors 75 and 77 effectively image the point 73 into the point 79. The cell 43 additionally has its length, cross-sectional dimensions and curvature of the mirrors 75 and 77 coordinated with the wavefront curvature of the incident composite beam 35 so that the collimation and focusing to a point 79 occurs, as described above.

The cell shown is designed for monitoring continuous gas flow which is directed into the cell through a tube 83 and taken away from the cell through a tube 85 (FIG. 1). The cell 45 operates in the same manner and has an output beam 87.

A planar mirror 89 and focusing mirror elements 91 and 93 are attached to the base plate 1 to image the output energy from both samples onto a single point infrared detector 95 that is also fixed to the base plate 1. These optical elements held by the base plate 1 form a second major optical component of the interferometer. Points 79 and 80 in space are imaged onto the detector 95. Foci 79 and 80 are spaced apart by the same distance that separates the foci 73 and 74, and all four foci remain the same distance above the base plate 1. A line through the points 73 and 74 is parallel to a line through the points 79 and 80. Also, these lines are parallel to the rods 3 and 4 and to the plate 1. The points 74 and 80 are similarly aligned. Thus, foci 73 and 74 can be made coincident with the foci 79 and 80, respectively, by sliding the platform 5.

An electrical output signal of the detector 95 is proportional to the desired interferogram of the sample material. The optical signal from the reference cell is optically subtracted from the optical signal output of the sample cell, leving an interferogram of the sample material only. Separate detectors could be used with each cell if electronic subtraction is provided but the single detector arrangement shows where subtraction occurs optically is preferred. This single detector arrangement avoids the problems of matching detectors and handling greater peak signal intensity.

The planar mirror 89 is provided in the path of both of the exit beams 81 and 85 to redirect them in order to keep the entire interferometer system in a small, compact package. Mirror elements 91 and 93 are elliptical in shape and tilted so as to focus their respective exit beams 81 and 87 onto the single detector 95 with a minimum amount of distortion and aberration. The conjugate foci of the mirrors 91 and 93 lie at the detector 95 and the points 79 and 80.

The focusing mirror elements 21, 39 and 41, previously described, are preferably in the shape of toroids, with one advantage of minimizing aberrations and distortion imparted thereby. The mirror surfaces 35, 31, 33, 49 and 51 and highly planar and serve the purpose of changing the direction of the energy beams in which paths they are positioned. Of course, focusing mirror elements can be substituted for these planar mirrors in other arrangements. The planar mirror element 31 is fixed parallel with the beam splitter surface 13. The oscillating mirror 33 is reciprocated in a direction perpendicular to the beam splitting surface 13 and remains parallel to the surface 13.

It will also be noticed that the optical system has an overall optical axis on which the beam splitting surface 13 lies. The cells 43 and 45 and their illuminating composite beams are parallel to this optical axis but on opposite sides thereof. When it is stated that the composite beams 35 and 37 are parallel to each other after leaving the mirror surfaces 49 and 51, respectively, it is meant that the central rays thereof are parallel to one another. Furthermore, the optical arrangements described results in the two composite beams 35 and 37 being spatially separated from each other and from all other beams.

It will be noticed that because of the parallel relationship of the mirrors 31 and 33 with the beam splitting surface 13, the angles of incidence and reflection of all light beams from the beam splitting surface 13 and the mirrors 31 and 33 will be the same angle $\theta$. The small value of the angle $\theta$ and the small distance of movement of the mirror 33 assures coaxial alignment of maximum overlap of the two components of each of the composite beams 35 and 37.

An interferometer has been described for use with polychromatic electromagnetic energy but it will be understood, of course, that the interferometer described is also useful with a coherent light source. Such an interferometer also may be used to advantage in applications other than spectroscopy, wherever interferometers are customarily employed.

Figure 3:
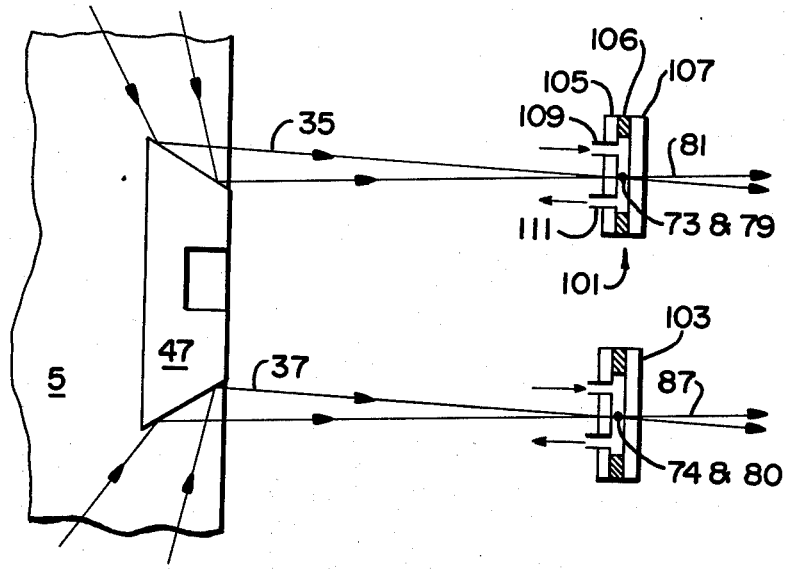
FIG. 3 shows in modified form a portion of the optical system illustrated in FIGS. 1 and 2.

Referring to FIG. 3, two different fluid containing cells 101 and 103 are provided in the composite illuminating beams 35 and 37, respectively. These cells are considerably thinner than those of FIG. 2 and are designed for holding liquid materials. Referring to cell 101 as typical of the structure of both of the cells illustrated in FIG. 3, two transparent plates 105 and 107 are held apart in parallel relationship to one another by a gasket 106. The windows 105 and 107 are optically planar and for most applications are held apart only by a fraction of a millimeter. Very little liquid is required for the radiation to pass through, in most circumstances, since the liquid is many times more absorptive to certain radiation frequencies than gaseous material for which the larger cells of FIG. 2 are designed. Small openings 109 and 111 through the glass plate 105 provide a means for introducing and withdrawing liquid from between the transparent plates 105 and 107.

The type of cell illustrated in FIG. 3 can, as well as the cells illustrated in FIG. 2, be utilized in a continuous process line wherein fluids are continuously passing through the cells while interferometric tests are being conducted on the fluids at periodic intervals. The results of such tests may then be utilized to effect changes in processes affecting the composition of the fluids.

For the type of cell illustrated in FIG. 3, the illuminating optics supporting platform 5 is moved in a direction toward the detector optics mounted in a fixed relationship to the base plate 11, as is illustrated in the comparison of the relative positions thereof shown in FIG. 2 and 3. In FIG. 3, the point focus 73 of the light beam 35 is made to be coincident with the point in space 79 that is imaged onto the detector 95. This coincidence must be an actual one and thus must take into account any refraction operating on the radiation by the transparent members 105 and 107 of the fluid cell 101. Although this point focus is shown in the middle of the cell 101, this need not be the relative position therewith since the cell 101 can be moved any where along the illuminating beam 35 as long as the energy of the beam passes through the liquid of interest. What has been described for the cell 101 and light beam 35 also applies to the cell 103 within the illuminating light beam 37. Movement of the platform 5 effects the same adjustment in each of the illuminating beams 35 and 37 at the same time.

The description hereinabove has referred to various "point" foci and a "point" radiation detector. It is to be understood that "point" as used herein is a small finite area. A specific detector for use herein has a radiation sensitive area of square shape with dimensions of about 20 mils on a side. Each "point" focus in the foregoing description has a size in the same order of magnitude.

In the specific description above, the cell illuminating optics have been made slidable while the detector and associated optics are fixed in position with respect to the sample and reference cells. However, the detector and its optics can in principal be made slidable while the illuminating optics are held fixed with respect to the sample and reference cells. Whichever arrangement is most convenient may be implemented.

Thus, an example of an improved interferometer which develops two composite output beams has been described. Of course, this is only exemplary of the present invention which is entitled to protection within the full scope of the appended claims.

I claim:

1. An optical system for examining material, comprising:
    means including a first optical system for forming two spaced apart electromagnetic energy illuminating beams having axes parallel to one another and each brought to a point focus that is fixed with respect to the first optical means, thereby to form two point foci that remain fixed at a given distance apart from each other,
    means including a second optical system for imaging two points in space said fixed distance apart onto at least one electromagnetic energy detector, and
    means maintaining the fixed focus of said two parallel beams fixed for moving said first and second optical means with respect to each other in a straight line direction parallel to said focused beams and through a distance that includes a coincidence of each of the point foci of said two beams with one of said two points in space, whereby difference sized materials may be positioned in the path of said parallel beams and an output beam therefrom accurately focused onto said detecting means.

2. The optical system according to claim 1 which additionally comprises a fluid containing cell positioned in the path of each of said two focused beams, each of said cells including a fluid chamber having optically transparent apertures on opposite walls thereof and means within each of the cells for imaging points at one aperture into points at the other aperture, each of said cells being positioned so that the point focus of its focused illuminating beam is coincident with one aperture thereof and one of said points in space is located at the output aperture thereof.

3. The optical system according to claim 1 which additionally comprises a liquid containing cell in the path of each of said focused beams, wherein said moving means is additionally positioned to make each focal point coincident with its associated one of said two points in space, each of said liquid containing cells including two parallel optically transparent members having a space therebetween for containing the liquid to be examined and being positioned with their respective illuminating beam passing directly therethrough.

4. The optical system according to claim 1 wherein said moving means comprises:
    a stationary frame having said second optical system imaging means fixedly mounted thereon,
    a platform upon which said first optical system forming means is mounted, and
    means for providing linear motion of said platform with respect to said base frame in a direction varying the distance separating said illuminating beam foci and said two points in space.

5. The optical system according to claim 1 wherein said first optical system forming means forms said two point foci along a line that is parallel to a line on which said two points in space are located, and further wherein said moving means maintains these lines parallel over a traveled distance that includes the simultaneous superposition of said point foci and said positions.

6. An optical system according to claim 1 wherein said first optical system includes an interferometer that comprises:
    a source of an electromagnetic energy beam,
    means splitting said beam into two substantially equal intensity components,
    means combining said components in a manner forming said two spaced apart electromagnetic energy illuminating beams having modulations of opposite phase.

* * * * *